US008608723B2

(12) United States Patent
Lev et al.

(10) Patent No.: US 8,608,723 B2
(45) Date of Patent: Dec. 17, 2013

(54) FLUID TRANSFER DEVICES WITH SEALING ARRANGEMENT

(75) Inventors: Nimrod Lev, Savion (IL); Niv Ben Shalom, Netanya (IL)

(73) Assignee: Medimop Medical Projects Ltd., Ra'anana (IL)

( * ) Notice: Subject to any disclaimer, the term of this patent is extended or adjusted under 35 U.S.C. 154(b) by 0 days.

(21) Appl. No.: 13/505,790

(22) PCT Filed: Oct. 19, 2010

(86) PCT No.: PCT/IL2010/000854
§ 371 (c)(1),
(2), (4) Date: May 3, 2012

(87) PCT Pub. No.: WO2011/058545
PCT Pub. Date: May 19, 2011

(65) Prior Publication Data

US 2012/0220978 A1 Aug. 30, 2012

(30) Foreign Application Priority Data

Nov. 12, 2009 (IL) .......................................... 202069

(51) Int. Cl.
*A61B 19/00* (2006.01)

(52) U.S. Cl.
USPC ............ 604/414; 604/415; 604/416; 604/403

(58) Field of Classification Search
USPC .......................................................... 604/414
See application file for complete search history.

(56) References Cited

U.S. PATENT DOCUMENTS

| | | | |
|---|---|---|---|
| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |
| 2,968,497 | A | 1/1961 | Treleman |
| 3,059,643 | A | 10/1962 | Barton |
| D198,499 | S | 6/1964 | Harautuneian |

(Continued)

FOREIGN PATENT DOCUMENTS

| | | | |
|---|---|---|---|
| DE | 1913926 | A1 | 9/1970 |
| DE | 4122476 | A1 | 1/1993 |

(Continued)

OTHER PUBLICATIONS

U.S. Appl. No. 13/522,410 by Lev, filed Jul. 16, 2012.

(Continued)

*Primary Examiner* — Leslie Deak
*Assistant Examiner* — Sara Sass
(74) *Attorney, Agent, or Firm* — Panitch Schwarze Belisario & Nadel LLP

(57) ABSTRACT

The present invention is directed toward fluid transfer devices including a vial adapter having a top wall and a cannula with a cannula tip, and an elastic O-ring like sealing element sealingly encircling the cannula and initially disposed towards the cannula tip and spaced apart from the top wall, the sealing element being brought into initial contact with the vial stopper subsequent to the cannula tip contacting the vial stopper at a puncture site and thereafter being slidingly urged towards the top wall and continuously sealing the puncture site during snap fit mounting the vial adapter on the vial.

10 Claims, 8 Drawing Sheets

(56) References Cited

U.S. PATENT DOCUMENTS

| | | | |
|---|---|---|---|
| 3,484,849 | A | 12/1969 | Huebner et al. |
| 3,618,637 | A | 11/1971 | Santomieri |
| 3,757,981 | A | 9/1973 | Harris, Sr. et al. |
| 3,826,261 | A | 7/1974 | Killinger |
| 3,885,607 | A | 5/1975 | Peltier |
| 3,957,052 | A | 5/1976 | Topham |
| 3,977,555 | A | 8/1976 | Larson |
| 3,993,063 | A | 11/1976 | Larrabee |
| 4,020,839 | A | 5/1977 | Klapp |
| 4,051,852 | A | 10/1977 | Villari |
| 4,109,670 | A | 8/1978 | Slagel |
| 4,187,848 | A | 2/1980 | Taylor |
| 4,210,173 | A | 7/1980 | Choksi et al. |
| D257,286 | S | 10/1980 | Folkman |
| 4,253,501 | A | 3/1981 | Ogle |
| 4,296,786 | A | 10/1981 | Brignola |
| 4,314,586 | A | 2/1982 | Folkman |
| 4,328,802 | A | 5/1982 | Curley et al. |
| D267,199 | S | 12/1982 | Koenig |
| 4,376,634 | A | 3/1983 | Prior et al. |
| D271,421 | S | 11/1983 | Fetterman |
| 4,434,823 | A | 3/1984 | Hudspith |
| 4,475,915 | A | 10/1984 | Sloane |
| 4,493,348 | A | 1/1985 | Lemmons |
| 4,505,709 | A | 3/1985 | Froning et al. |
| 4,507,113 | A | 3/1985 | Dunlap |
| D280,018 | S | 8/1985 | Scott |
| 4,532,969 | A | 8/1985 | Kwaan |
| 4,564,054 | A | 1/1986 | Gustavsson |
| 4,576,211 | A | 3/1986 | Valentini et al. |
| 4,588,396 | A | 5/1986 | Stroebel et al. |
| 4,588,403 | A | 5/1986 | Weiss et al. |
| D284,603 | S | 7/1986 | Loignon |
| 4,604,093 | A | 8/1986 | Brown et al. |
| 4,607,671 | A | 8/1986 | Aalto et al. |
| 4,614,437 | A | 9/1986 | Buehler |
| 4,638,975 | A | 1/1987 | Iuchi et al. |
| 4,639,019 | A | 1/1987 | Mittleman |
| 4,667,927 | A | 5/1987 | Oscarsson |
| 4,676,530 | A | 6/1987 | Nordgren et al. |
| 4,683,975 | A | 8/1987 | Booth et al. |
| 4,697,622 | A | 10/1987 | Swift et al. |
| 4,721,133 | A | 1/1988 | Sundblom |
| 4,729,401 | A | 3/1988 | Raines |
| 4,735,608 | A | 4/1988 | Sardam |
| 4,743,229 | A | 5/1988 | Chu |
| 4,743,243 | A | 5/1988 | Vaillancourt |
| 4,758,235 | A | 7/1988 | Tu |
| 4,759,756 | A | 7/1988 | Forman et al. |
| 4,778,447 | A | 10/1988 | Velde et al. |
| 4,787,898 | A | 11/1988 | Raines |
| 4,797,898 | A | 1/1989 | Martinez |
| 4,834,152 | A | 5/1989 | Howson et al. |
| 4,865,592 | A | 9/1989 | Rycroft |
| 4,909,290 | A | 3/1990 | Coccia |
| 4,967,797 | A | 11/1990 | Manska |
| D314,050 | S | 1/1991 | Sone |
| 4,997,430 | A | 3/1991 | Van der Heiden et al. |
| 5,035,686 | A | 7/1991 | Crittenden et al. |
| 5,041,105 | A | 8/1991 | D'Alo et al. |
| 5,045,066 | A | 9/1991 | Scheuble et al. |
| 5,049,129 | A | 9/1991 | Zdeb et al. |
| 5,053,015 | A | 10/1991 | Gross |
| 5,061,248 | A | 10/1991 | Sacco |
| 5,088,996 | A | 2/1992 | Kopfer et al. |
| 5,096,575 | A | 3/1992 | Cosack |
| 5,104,387 | A | 4/1992 | Pokorney et al. |
| 5,113,904 | A | 5/1992 | Aslanian |
| 5,122,124 | A | 6/1992 | Novacek et al. |
| 5,125,908 | A | 6/1992 | Cohen |
| 5,171,230 | A | 12/1992 | Eland et al. |
| 5,201,705 | A | 4/1993 | Berglund et al. |
| 5,201,717 | A | 4/1993 | Wyatt et al. |
| 5,203,771 | A | 4/1993 | Melker et al. |
| 5,203,775 | A | 4/1993 | Frank et al. |
| 5,211,638 | A | 5/1993 | Dudar et al. |
| 5,232,029 | A | 8/1993 | Knox et al. |
| 5,232,109 | A | 8/1993 | Tirrell et al. |
| 5,247,972 | A | 9/1993 | Tetreault |
| 5,269,768 | A | 12/1993 | Cheung |
| 5,270,219 | A | 12/1993 | DeCastro et al. |
| 5,279,576 | A | 1/1994 | Loo et al. |
| 5,288,290 | A | 2/1994 | Brody |
| 5,304,163 | A | 4/1994 | Bonnici et al. |
| 5,312,377 | A | 5/1994 | Dalton |
| 5,328,474 | A | 7/1994 | Raines |
| D349,648 | S | 8/1994 | Tirrell et al. |
| 5,334,163 | A | 8/1994 | Sinnett |
| 5,334,179 | A | 8/1994 | Poli et al. |
| 5,342,346 | A | 8/1994 | Honda et al. |
| 5,344,417 | A | 9/1994 | Wadsworth, Jr. |
| 5,350,372 | A | 9/1994 | Ikeda et al. |
| 5,364,386 | A | 11/1994 | Fukuoka et al. |
| 5,364,387 | A | 11/1994 | Sweeney |
| 5,374,264 | A | 12/1994 | Wadsworth, Jr. |
| 5,385,547 | A | 1/1995 | Wong et al. |
| 5,397,303 | A | 3/1995 | Sancoff et al. |
| 5,429,614 | A | 7/1995 | Fowles et al. |
| 5,433,330 | A | 7/1995 | Yatsko et al. |
| 5,445,630 | A | 8/1995 | Richmond |
| 5,445,631 | A | 8/1995 | Uchida |
| 5,451,374 | A | 9/1995 | Molina |
| 5,454,805 | A | 10/1995 | Brony |
| 5,464,111 | A | 11/1995 | Vacek et al. |
| 5,464,123 | A | 11/1995 | Scarrow |
| 5,466,219 | A | 11/1995 | Lynn et al. |
| 5,466,220 | A | 11/1995 | Brenneman |
| 5,470,327 | A | 11/1995 | Helgren et al. |
| 5,478,337 | A | 12/1995 | Okamoto et al. |
| 5,492,147 | A | 2/1996 | Challender et al. |
| 5,505,714 | A | 4/1996 | Dassa et al. |
| 5,509,433 | A | 4/1996 | Paradis |
| 5,520,659 | A | 5/1996 | Hedges |
| 5,526,853 | A | 6/1996 | McPhee et al. |
| 5,527,306 | A | 6/1996 | Haining |
| 5,531,695 | A | 7/1996 | Swisher |
| 5,554,128 | A | 9/1996 | Hedges |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,641,010 | A | 6/1997 | Maier |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,755,696 | A | 5/1998 | Caizza |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,806,831 | A | 9/1998 | Paradis |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |

(56) References Cited

U.S. PATENT DOCUMENTS

| | | | |
|---|---|---|---|
| 5,839,715 | A | 11/1998 | Leinsing |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,899,468 | A | 5/1999 | Apps et al. |
| 5,902,280 | A | 5/1999 | Powles et al. |
| 5,902,298 | A | 5/1999 | Niedospial, Jr. et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,944,700 | A | 8/1999 | Nguyen et al. |
| 5,954,104 | A | 9/1999 | Daubert et al. |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| 6,070,623 | A | 6/2000 | Aneas |
| 6,071,270 | A | 6/2000 | Fowles et al. |
| 6,080,132 | A | 6/2000 | Cole et al. |
| 6,089,541 | A | 7/2000 | Weinheimer et al. |
| 6,090,091 | A | 7/2000 | Fowles et al. |
| 6,090,093 | A | 7/2000 | Thibault et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| 6,139,534 | A | 10/2000 | Niedospial, Jr. et al. |
| 6,142,446 | A | 11/2000 | Leinsing |
| 6,156,025 | A | 12/2000 | Niedospial, Jr. et al. |
| 6,159,192 | A | 12/2000 | Fowles et al. |
| 6,168,037 | B1 | 1/2001 | Grimard |
| 6,171,293 | B1 | 1/2001 | Rowley et al. |
| 6,173,852 | B1 | 1/2001 | Browne |
| 6,174,304 | B1 | 1/2001 | Weston |
| 6,206,861 | B1 | 3/2001 | Mayer |
| 6,221,041 | B1 | 4/2001 | Russo |
| 6,221,054 | B1 | 4/2001 | Martin et al. |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,299,131 | B1 | 10/2001 | Ryan |
| 6,343,629 | B1 | 2/2002 | Wessman et al. |
| 6,348,044 | B1 | 2/2002 | Coletti et al. |
| 6,358,236 | B1 | 3/2002 | DeFoggi et al. |
| 6,364,866 | B1 | 4/2002 | Furr et al. |
| 6,378,576 | B2 | 4/2002 | Thibault et al. |
| 6,378,714 | B1 | 4/2002 | Jansen et al. |
| 6,379,340 | B1 | 4/2002 | Zinger et al. |
| 6,382,442 | B1 | 5/2002 | Thibault et al. |
| 6,408,897 | B1 | 6/2002 | Laurent et al. |
| 6,409,708 | B1 | 6/2002 | Wessman |
| 6,453,956 | B2 | 9/2002 | Safabash |
| 6,474,375 | B2 | 11/2002 | Spero et al. |
| 6,478,788 | B1 | 11/2002 | Aneas |
| D468,015 | S | 12/2002 | Horppu |
| 6,499,617 | B1 | 12/2002 | Niedospial, Jr. et al. |
| 6,503,240 | B1 | 1/2003 | Niedospial, Jr. et al. |
| 6,503,244 | B2 | 1/2003 | Hayman |
| 6,524,278 | B1 | 2/2003 | Campbell et al. |
| 6,524,295 | B2 | 2/2003 | Daubert et al. |
| D472,316 | S | 3/2003 | Douglas et al. |
| 6,530,903 | B2 | 3/2003 | Wang et al. |
| 6,537,263 | B1 | 3/2003 | Aneas |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,572,591 | B2 | 6/2003 | Mayer |
| 6,575,955 | B2 | 6/2003 | Azzolini |
| 6,581,593 | B1 | 6/2003 | Rubin et al. |
| 6,582,415 | B1 | 6/2003 | Fowles et al. |
| 6,591,876 | B2 | 7/2003 | Safabash |
| 6,601,721 | B2 | 8/2003 | Jansen et al. |
| 6,626,309 | B1 | 9/2003 | Jansen et al. |
| 6,651,956 | B2 | 11/2003 | Miller |
| 6,652,509 | B1 | 11/2003 | Helgren et al. |
| D483,487 | S | 12/2003 | Harding et al. |
| D483,869 | S | 12/2003 | Tran et al. |
| 6,656,433 | B2 | 12/2003 | Sasso |
| 6,666,852 | B2 | 12/2003 | Niedospial, Jr. |
| 6,681,810 | B2 | 1/2004 | Weston |
| 6,681,946 | B1 | 1/2004 | Jansen et al. |
| 6,682,509 | B2 | 1/2004 | Lopez |
| 6,692,829 | B2 | 2/2004 | Stubler et al. |
| 6,695,829 | B2 | 2/2004 | Hellstrom et al. |
| 6,699,229 | B2 | 3/2004 | Zinger et al. |
| 6,706,031 | B2 | 3/2004 | Manera |
| 6,715,520 | B2 | 4/2004 | Andreasson et al. |
| 6,729,370 | B2 | 5/2004 | Norton et al. |
| 6,736,798 | B2 | 5/2004 | Ohkubo et al. |
| 6,745,998 | B2 | 6/2004 | Doyle |
| 6,746,438 | B1 | 6/2004 | Arnissolle |
| 6,752,180 | B2 | 6/2004 | Delay |
| D495,416 | S | 8/2004 | Dimeo et al. |
| D496,457 | S | 9/2004 | Prais et al. |
| 6,802,490 | B2 | 10/2004 | Leinsing et al. |
| 6,832,994 | B2 | 12/2004 | Niedospial, Jr. et al. |
| 6,852,103 | B2 | 2/2005 | Fuller et al. |
| 6,875,203 | B1 | 4/2005 | Fowles et al. |
| 6,875,205 | B2 | 4/2005 | Leinsing |
| 6,878,131 | B2 | 4/2005 | Novacek et al. |
| 6,890,328 | B2 | 5/2005 | Fowles et al. |
| 6,901,975 | B2 | 6/2005 | Aramata et al. |
| 6,945,417 | B2 | 9/2005 | Jansen et al. |
| 6,948,522 | B2 | 9/2005 | Newbrough et al. |
| 6,949,086 | B2 | 9/2005 | Ferguson et al. |
| 6,957,745 | B2 | 10/2005 | Thibault et al. |
| RE38,996 | E | 2/2006 | Crawford et al. |
| 6,994,315 | B2 | 2/2006 | Ryan et al. |
| 6,997,917 | B2 | 2/2006 | Niedospial, Jr. et al. |
| 7,024,968 | B2 | 4/2006 | Raudabough et al. |
| 7,074,216 | B2 | 7/2006 | Fowles et al. |
| 7,083,600 | B2 | 8/2006 | Meloul |
| 7,086,431 | B2 | 8/2006 | D'Antonio et al. |
| 7,100,890 | B2 | 9/2006 | Cote, Sr. et al. |
| 7,150,735 | B2 | 12/2006 | Hickle |
| 7,192,423 | B2 | 3/2007 | Wong |
| 7,195,623 | B2 | 3/2007 | Burroughs et al. |
| 7,294,122 | B2 | 11/2007 | Kubo et al. |
| 7,306,199 | B2 | 12/2007 | Leinsing et al. |
| D561,348 | S | 2/2008 | Zinger et al. |
| 7,326,194 | B2 | 2/2008 | Zinger et al. |
| 7,350,764 | B2 | 4/2008 | Raybuck |
| 7,354,422 | B2 | 4/2008 | Riesenberger et al. |
| 7,354,427 | B2 | 4/2008 | Fangrow |
| 7,425,209 | B2 | 9/2008 | Fowles et al. |
| 7,435,246 | B2 | 10/2008 | Zihlmann |
| 7,452,348 | B2 | 11/2008 | Hasegawa |
| 7,470,257 | B2 | 12/2008 | Norton et al. |
| 7,470,265 | B2 | 12/2008 | Brugger et al. |
| 7,472,932 | B2 | 1/2009 | Weber et al. |
| 7,488,297 | B2 | 2/2009 | Flaherty |
| 7,491,197 | B2 | 2/2009 | Jansen et al. |
| 7,497,848 | B2 | 3/2009 | Leinsing et al. |
| 7,523,967 | B2 | 4/2009 | Steppe |

(56) References Cited

U.S. PATENT DOCUMENTS

| | | | |
|---|---|---|---|
| 7,530,546 | B2 | 5/2009 | Ryan et al. |
| D595,420 | S | 6/2009 | Suzuki et al. |
| D595,421 | S | 6/2009 | Suzuki et al. |
| 7,540,863 | B2 | 6/2009 | Haindl |
| 7,540,865 | B2 | 6/2009 | Griffin et al. |
| D595,862 | S | 7/2009 | Suzuki et al. |
| D595,863 | S | 7/2009 | Suzuki et al. |
| 7,611,487 | B2 | 11/2009 | Woehr et al. |
| 7,611,502 | B2 | 11/2009 | Daly |
| 7,615,041 | B2 | 11/2009 | Sullivan et al. |
| 7,628,779 | B2 | 12/2009 | Aneas |
| 7,632,261 | B2 | 12/2009 | Zinger et al. |
| D608,900 | S | 1/2010 | Giraud et al. |
| 7,654,995 | B2 | 2/2010 | Warren et al. |
| 7,695,445 | B2 | 4/2010 | Yuki |
| D616,090 | S | 5/2010 | Kawamura |
| 7,713,247 | B2 | 5/2010 | Lopez |
| 7,717,886 | B2 | 5/2010 | Lopez |
| 7,722,090 | B2 | 5/2010 | Burton et al. |
| D616,984 | S | 6/2010 | Gilboa |
| 7,731,678 | B2 | 6/2010 | Tennican et al. |
| 7,743,799 | B2 | 6/2010 | Mosler et al. |
| 7,758,082 | B2 | 7/2010 | Weigel et al. |
| 7,762,524 | B2 | 7/2010 | Cawthon et al. |
| 7,766,304 | B2 | 8/2010 | Phillips |
| 7,771,383 | B2 | 8/2010 | Truitt et al. |
| 7,799,009 | B2 | 9/2010 | Niedospial, Jr. et al. |
| 7,803,140 | B2 | 9/2010 | Fangrow, Jr. |
| D627,216 | S | 11/2010 | Fulginiti |
| D630,732 | S | 1/2011 | Lev et al. |
| 7,862,537 | B2 | 1/2011 | Zinger et al. |
| 7,867,215 | B2 | 1/2011 | Akerlund et al. |
| 7,879,018 | B2 | 2/2011 | Zinger et al. |
| 7,900,659 | B2 | 3/2011 | Whitley et al. |
| D637,713 | S | 5/2011 | Nord et al. |
| D644,104 | S | 8/2011 | Maeda et al. |
| 7,993,328 | B2 | 8/2011 | Whitley |
| 8,016,809 | B2 | 9/2011 | Zinger et al. |
| 8,025,653 | B2 | 9/2011 | Capitaine et al. |
| 8,029,472 | B2 | 10/2011 | Leinsing et al. |
| 8,038,123 | B2 | 10/2011 | Ruschke et al. |
| 8,066,688 | B2 | 11/2011 | Zinger et al. |
| 8,070,739 | B2 | 12/2011 | Zinger et al. |
| 8,096,525 | B2 | 1/2012 | Ryan |
| 8,105,314 | B2 | 1/2012 | Fangrow, Jr. |
| D655,017 | S | 2/2012 | Mosler et al. |
| 8,157,784 | B2 | 4/2012 | Rogers |
| 8,167,863 | B2 | 5/2012 | Yow |
| 8,172,824 | B2 | 5/2012 | Pfeifer et al. |
| 8,177,768 | B2 | 5/2012 | Leinsing |
| 8,182,452 | B2 | 5/2012 | Mansour et al. |
| 8,197,459 | B2 | 6/2012 | Jansen et al. |
| 8,211,069 | B2 | 7/2012 | Fangrow, Jr. |
| 8,225,959 | B2 | 7/2012 | Lambrecht |
| 8,241,268 | B2 | 8/2012 | Whitley |
| 8,262,628 | B2 | 9/2012 | Fangrow, Jr. |
| D669,980 | S | 10/2012 | Lev et al. |
| 8,287,513 | B2 | 10/2012 | Ellstrom et al. |
| D674,088 | S | 1/2013 | Lev et al. |
| 8,480,646 | B2 | 7/2013 | Nord et al. |
| 8,551,067 | B2 | 10/2013 | Zinger et al. |
| 2001/0000347 | A1 | 4/2001 | Hellstrom et al. |
| 2001/0025671 | A1 | 10/2001 | Safabash |
| 2001/0029360 | A1 | 10/2001 | Miyoshi et al. |
| 2001/0051793 | A1 | 12/2001 | Weston |
| 2002/0017328 | A1 | 2/2002 | Loo |
| 2002/0066715 | A1 | 6/2002 | Niedospial |
| 2002/0087118 | A1 | 7/2002 | Reynolds et al. |
| 2002/0087141 | A1 | 7/2002 | Zinger et al. |
| 2002/0087144 | A1 | 7/2002 | Zinger et al. |
| 2002/0121496 | A1 | 9/2002 | Thiebault et al. |
| 2002/0123736 | A1 | 9/2002 | Fowles et al. |
| 2002/0127150 | A1 | 9/2002 | Sasso |
| 2002/0173752 | A1 | 11/2002 | Polzin |
| 2002/0193777 | A1 | 12/2002 | Aneas |
| 2003/0036725 | A1 | 2/2003 | Lavi et al. |
| 2003/0100866 | A1 | 5/2003 | Reynolds |
| 2003/0120209 | A1 | 6/2003 | Jensen et al. |
| 2003/0153895 | A1 | 8/2003 | Leinsing |
| 2003/0195479 | A1 | 10/2003 | Kuracina et al. |
| 2003/0199846 | A1 | 10/2003 | Fowles et al. |
| 2003/0199847 | A1 | 10/2003 | Akerlund et al. |
| 2004/0024354 | A1 | 2/2004 | Reynolds |
| 2004/0044327 | A1 | 3/2004 | Hasegawa |
| 2004/0073189 | A1 | 4/2004 | Wyatt et al. |
| 2004/0153047 | A1 | 8/2004 | Blank et al. |
| 2004/0181192 | A1 | 9/2004 | Cuppy |
| 2004/0217315 | A1 | 11/2004 | Doyle |
| 2004/0236305 | A1* | 11/2004 | Jansen et al. .................. 604/411 |
| 2005/0055008 | A1 | 3/2005 | Paradis et al. |
| 2005/0124964 | A1 | 6/2005 | Niedospial et al. |
| 2005/0137566 | A1 | 6/2005 | Fowles et al. |
| 2005/0148994 | A1 | 7/2005 | Leinsing |
| 2005/0159724 | A1 | 7/2005 | Enerson |
| 2005/0261637 | A1 | 11/2005 | Miller |
| 2006/0030832 | A1 | 2/2006 | Niedospial et al. |
| 2006/0079834 | A1 | 4/2006 | Tennican et al. |
| 2006/0089594 | A1 | 4/2006 | Landau |
| 2006/0089603 | A1 | 4/2006 | Truitt et al. |
| 2006/0106360 | A1 | 5/2006 | Wong |
| 2006/0135948 | A1 | 6/2006 | Varma |
| 2006/0253084 | A1 | 11/2006 | Nordgren |
| 2007/0060904 | A1 | 3/2007 | Vedrine et al. |
| 2007/0079894 | A1 | 4/2007 | Kraus et al. |
| 2007/0083164 | A1 | 4/2007 | Barrelle et al. |
| 2007/0088252 | A1 | 4/2007 | Pestotnik et al. |
| 2007/0088293 | A1 | 4/2007 | Fangrow |
| 2007/0088313 | A1 | 4/2007 | Zinger et al. |
| 2007/0106244 | A1 | 5/2007 | Mosler et al. |
| 2007/0112324 | A1 | 5/2007 | Hamedi-Sangsari |
| 2007/0156112 | A1 | 7/2007 | Walsh |
| 2007/0167904 | A1 | 7/2007 | Zinger et al. |
| 2007/0191760 | A1 | 8/2007 | Iguchi et al. |
| 2007/0191764 | A1 | 8/2007 | Zihlmann |
| 2007/0191767 | A1 | 8/2007 | Hennessy et al. |
| 2007/0219483 | A1 | 9/2007 | Kitani et al. |
| 2007/0244461 | A1 | 10/2007 | Fangrow |
| 2007/0244462 | A1 | 10/2007 | Fangrow |
| 2007/0244463 | A1 | 10/2007 | Warren et al. |
| 2007/0255202 | A1 | 11/2007 | Kitani et al. |
| 2007/0265574 | A1 | 11/2007 | Tennican et al. |
| 2007/0265581 | A1 | 11/2007 | Funamura et al. |
| 2007/0270778 | A9 | 11/2007 | Zinger et al. |
| 2007/0287953 | A1 | 12/2007 | Ziv et al. |
| 2008/0009789 | A1 | 1/2008 | Zinger et al. |
| 2008/0009822 | A1 | 1/2008 | Enerson |
| 2008/0172024 | A1 | 7/2008 | Yow |
| 2008/0249479 | A1 | 10/2008 | Zinger et al. |
| 2008/0249498 | A1 | 10/2008 | Fangrow |
| 2008/0287905 | A1 | 11/2008 | Hiejima et al. |
| 2008/0312634 | A1 | 12/2008 | Helmerson et al. |
| 2009/0012492 | A1 | 1/2009 | Zihlmann |
| 2009/0054834 | A1 | 2/2009 | Zinger et al. |
| 2009/0082750 | A1 | 3/2009 | Denenburg et al. |
| 2009/0143758 | A1 | 6/2009 | Okiyama |
| 2009/0177177 | A1 | 7/2009 | Zinger et al. |
| 2009/0177178 | A1 | 7/2009 | Pedersen |
| 2009/0187140 | A1 | 7/2009 | Racz |
| 2009/0216212 | A1 | 8/2009 | Fangrow, Jr. |
| 2009/0267011 | A1* | 10/2009 | Hatton et al. ................. 251/279 |
| 2009/0299325 | A1 | 12/2009 | Vedrine et al. |
| 2009/0326506 | A1 | 12/2009 | Hasegawa et al. |
| 2010/0010443 | A1 | 1/2010 | Morgan et al. |
| 2010/0022985 | A1 | 1/2010 | Sullivan et al. |
| 2010/0030181 | A1 | 2/2010 | Helle et al. |
| 2010/0036319 | A1 | 2/2010 | Drake et al. |
| 2010/0076397 | A1 | 3/2010 | Reed et al. |
| 2010/0087786 | A1 | 4/2010 | Zinger et al. |
| 2010/0137827 | A1 | 6/2010 | Warren et al. |
| 2010/0168712 | A1 | 7/2010 | Tuckwell et al. |
| 2010/0179506 | A1 | 7/2010 | Shemesh et al. |
| 2010/0204670 | A1 | 8/2010 | Kraushaar et al. |
| 2010/0228220 | A1 | 9/2010 | Zinger et al. |
| 2010/0241088 | A1 | 9/2010 | Ranalletta et al. |

(56) References Cited

U.S. PATENT DOCUMENTS

| | | | |
|---|---|---|---|
| 2010/0286661 | A1 | 11/2010 | Raday et al. |
| 2010/0312220 | A1 | 12/2010 | Kalitzki |
| 2011/0054440 | A1 | 3/2011 | Lewis |
| 2011/0224640 | A1 | 9/2011 | Kuhn et al. |
| 2011/0230856 | A1 | 9/2011 | Kyle et al. |
| 2011/0264069 | A1 | 10/2011 | Bochenko |
| 2011/0276007 | A1 | 11/2011 | Denenburg |
| 2011/0319827 | A1 | 12/2011 | Leinsing et al. |
| 2012/0022469 | A1 | 1/2012 | Alpert |
| 2012/0053555 | A1 | 3/2012 | Ariagno et al. |
| 2012/0059346 | A1 | 3/2012 | Sheppard et al. |
| 2012/0078214 | A1 | 3/2012 | Finke et al. |
| 2012/0123382 | A1 | 5/2012 | Kubo |
| 2012/0215182 | A1 | 8/2012 | Mansour et al. |
| 2012/0220977 | A1 | 8/2012 | Yow |
| 2012/0220978 | A1 | 8/2012 | Lev et al. |
| 2012/0265163 | A1 | 10/2012 | Cheng et al. |
| 2012/0310203 | A1 | 12/2012 | Khaled et al. |
| 2013/0053814 | A1 | 2/2013 | Mueller-Beckhaus et al. |

FOREIGN PATENT DOCUMENTS

| | | | |
|---|---|---|---|
| DE | 19504413 | A1 | 8/1996 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 897708 | A2 | 2/1999 |
| EP | 0898951 | A2 | 3/1999 |
| EP | 960616 | A2 | 12/1999 |
| EP | 1008337 | A1 | 6/2000 |
| EP | 1029526 | A1 | 8/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1919432 | A1 | 5/2008 |
| EP | 1930038 | A2 | 6/2008 |
| EP | 2351548 | A1 | 8/2011 |
| EP | 2351549 | A1 | 8/2011 |
| FR | 2029242 | A5 | 10/1970 |
| FR | 2856660 | A1 | 12/2004 |
| FR | 2869795 | A1 | 11/2005 |
| FR | 2931363 | A1 | 11/2009 |
| GB | 1444210 | A | 7/1976 |
| JP | 4329954 | A | 11/1992 |
| JP | H08-000710 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2003-102807 | A | 4/2003 |
| JP | 2004-097253 | A | 4/2004 |
| JP | 2004-522541 | A | 7/2004 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0236191 | A2 | 5/2002 |
| WO | 03051423 | A2 | 6/2003 |
| WO | 2004041148 | A1 | 5/2004 |
| WO | 2005002492 | A1 | 1/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007105221 | A1 | 9/2007 |
| WO | 2009026443 | A2 | 2/2009 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012143921 | A1 | 10/2012 |

OTHER PUBLICATIONS

U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
U.S. Appl. No. 29/438,134 by Lev, filed Nov. 27, 2012.
U.S. Appl. No. 29/438,141 by Gilboa, filed Nov. 27, 2012.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/SiteCollectionDocuments/Recon/mixject%20product%20sheet.pfg; MIXJECT product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.

(56) References Cited

OTHER PUBLICATIONS

Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
U.S. Appl. No. 13/498,378 by Lev, filed Mar. 27, 2012.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
Int'l Search Report issued Aug. 16, 2012 in Int'l Application No. PCT/IL2012/000164.
U.S. Appl. No. 13/505,881 by Lev, filed May 3, 2012.
Int'l Search Report issued Jan. 22, 2013 in Int'l Application No. PCT/IL2012/000354.
Int'l Search Report issued Mar. 18, 2013 in Int'l Application No. PCT/IL2012/050516.
Int'l Search Report and Written Opinion issued Mar. 6, 2012 in Int'l Application No. PCT/IL2011/000834.
U.S. Appl. No. 13/883,289 by Lev, filed May 3, 2013.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
English translation of an Office Action issued Jun. 19, 2013 in JP Application No. 2012-531551.
Int'l Search Report issued Jul. 31, 2013 in Int'l Application No. PCT/IL2013/050313.
Int'l Search Report issued Jul. 26, 2013 in Int'l Application No. PCT/IL2013/050316.
Office Action issued Aug. 20, 2013 in U.S. Appl. No. 13/576,461 by Lev.
U.S. Appl. No. 14/005,751 by Denenburg, filed Sep. 17, 2013.
English translation of an Office Action issued Jul. 26, 2013 in JP Application No. 2012-538464.

* cited by examiner

FLUID TRANSFER DEVICES WITH SEALING ARRANGEMENT

CROSS-REFERENCE TO RELATED APPLICATION

This application is a Section 371 of International Application No. PCT/IL2010/000854, filed Oct. 19, 2010, which was published in the English language on May 19, 2011, under International Publication No. WO 2011/058545 A1, and the disclosure of which is incorporated herein by reference.

FIELD OF THE INVENTION

The invention relates to fluid transfer devices for use with medicinal vessels hermetically sealed by an elastic vial stopper and containing a liquid or powder medicament.

BACKGROUND OF THE INVENTION

Fluid transfer devices including a vial adapter with a pointed cannula for snap fitting on an aforesaid medicinal vessel or vial are now commonly employed for liquid drug reconstitution and administration purposes. Such devices include inter alia female vial adapters, male vial adapters, Applicant's MIXJECT® fluid transfer device, Applicant's MIX2VIAL® fluid transfer assemblage, and the like. Tears may be formed in a vial stopper during snap fitting of a fluid transfer device thereonto leading to leakage of liquid contents during injection into and aspiration from the vial. Tears also complicate liquid drug reconstitution in fluid transfer assemblages, for example, the aforesaid MIX2VIAL® fluid transfer assemblage, assisted by a negative pressure of a powder containing vial.

Tears often result from an initial inaccurate alignment between a fluid transfer device and a vial due to the latter centering the former as it snap fits thereonto such that the fluid transfer device is concentrically snap fit mounted onto the vial. Initial inaccurate alignment may be in the form of either a skewed alignment between a fluid transfer device and a vial or an eccentric alignment therebetween particularly in the case of a vial adapter with a flared skirt for assisting in guiding a vial adapter onto a vial. But tears may still occur even in the case of an initial concentric alignment between a fluid transfer device and a vial due to the constitution of an elastic vial stopper.

US Publication No. 2004/0236305 entitled Fluid Transfer Device illustrates and describes a fluid transfer device for mounting on a medicinal vessel. The fluid transfer device includes a receiving cap and a piercing mandril for piercing an elastic stopper. Relative to its direction of piercing, the piercing mandril has a front piercing portion and rear sealing portion which is of greater diameter for sealing a tear in a stopper. An alternative embodiment includes providing a rear sealing portion with a fixedly mounted elastic O-ring for providing additional sealing capability.

U.S. Pat. No. 5,374,264 entitled Universal Fitting for Inoculation Receptacles illustrates and describes a fluid transfer device for mounting on a medicinal vessel. The fluid transfer device includes a vial adapter with a top wall, a skirt and a pointed cannula provided with a sheath for folding accordion like as it is compressed between the top wall and a medicinal vessel's elastic stopper.

SUMMARY OF THE INVENTION

The present invention is directed toward fluid transfer devices with a sealing arrangement for preventing leakage from medicament containing medicinal vessels or vials. The fluid transfer devices include a vial adapter having a top wall, a downward depending skirt with flex members for snap fitting onto a vial having a vial stopper, a pointed tubular cannula for piercing the vial stopper while snap fitting the vial adapter onto the vial, and a flow channel in flow communication with the cannula for enabling external flow communication with the vial interior. The vial adapter can have a general cylindrical shape skirt or a so-called flared skirt for assisting in guidance onto a vial.

The fluid transfer devices each include an elastic O-ring like sealing element disposed along a cannula and sealingly encircling same. A sealing element is intended to seal the immediate vicinity surrounding a puncture site of its cannula as the sealing element contacts a vial stopper and to be slidingly urged along a cannula towards a top wall as a fluid transfer device snap fits onto a vial to maintain continuous sealing contact with a puncture site thereby sealing any tears resulting from snap fit mounting irrespective the reason for their formation. The sealing element is typically axially compressed between a fluid transfer device's top wall and a vial stopper on full snap fit mounting of the former on the latter whereupon the sealing element extends radially outward to cover a greater area on the uppermost stopper surface.

The initial location of a sealing element along a cannula depends on whether a sealing element is intended to prevent negative pressure leakage or liquid leakage. In the former instance, a sealing element is necessarily disposed along a cannula towards its cannula tip such that it contacts a vial stopper prior to stopper perforation. In the latter instance, a sealing element may be disposed further from a cannula tip. Fluid transfer devices with proportionally sized sealing elements can be designed for use with different standard sizes of vials, for example, 13 mm, 20 mm, and larger. The present invention can be readily applied to conventional fluid transfer devices including a vial adapter with a pointed cannula.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
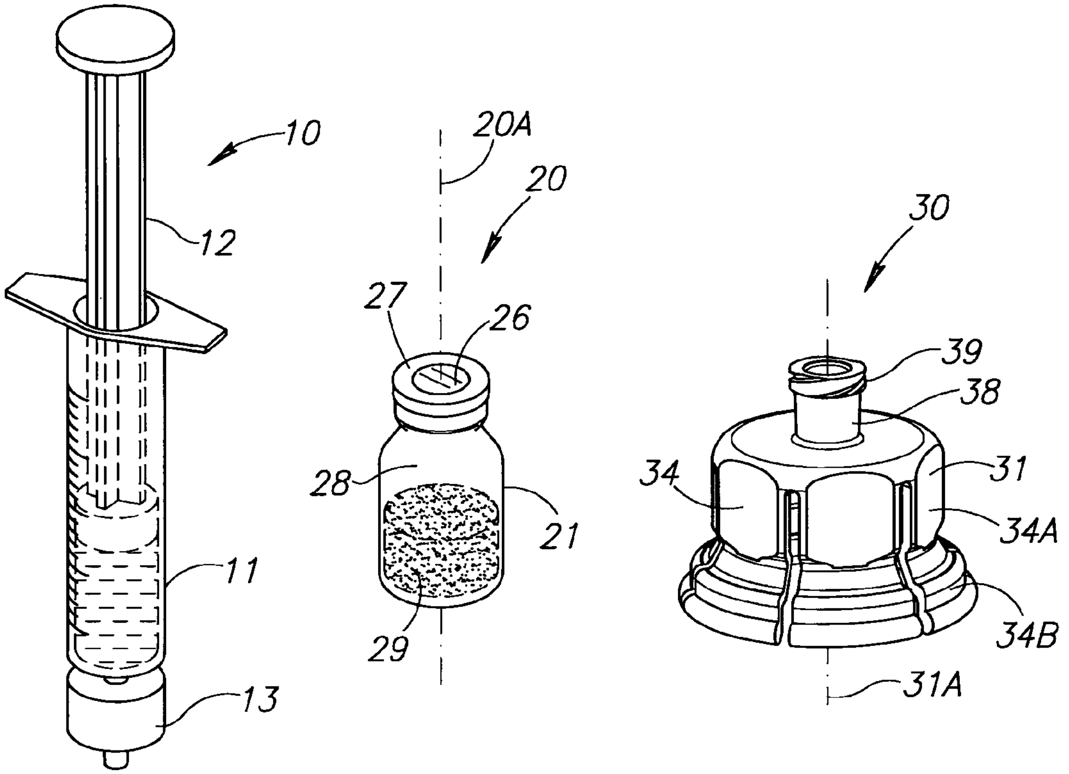
FIG.1 (PRIOR ART)
FIG. 1 shows a pictorial representation of a syringe, a vial having a vial stopper, and a conventional vial adapter.
Figure 2:
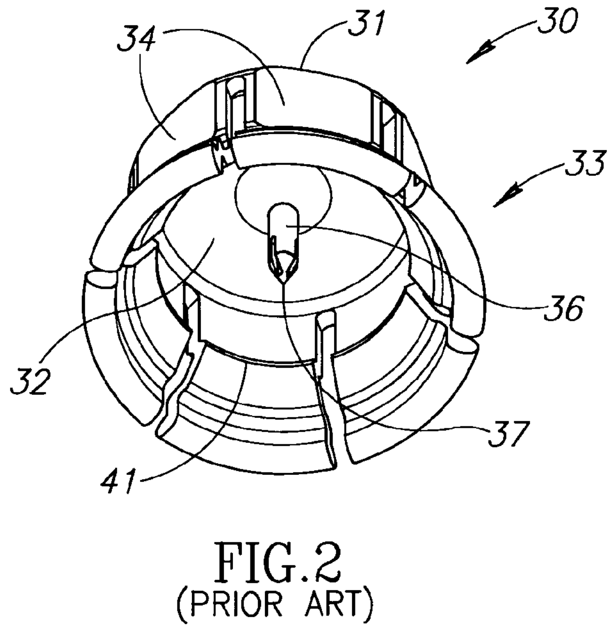
FIG.2 (PRIOR ART)
FIG. 2 is a bottom perspective view of FIG. 1's vial adapter.

FIG. 1 shows a syringe 10 constituting a source of physiological fluid, a vial 20 constituting a medicinal vessel and a fluid transfer device 30 constituted by a female vial adapter for use with the syringe 10 and the vial 20, all as known in the art. The syringe 10 includes a barrel 11 with a plunger 12 and a male Luer lock connector 13. The syringe 10 can be formed with other types of male connectors. The vial 20 has a longitudinal vial axis 20A and includes a vial body 21 with a vial rim 22 and a narrow diameter neck 23 intermediate the vial body 21 and the vial rim 22. The vial rim 22 defines a vial opening 24 hermetically sealed by an elastic vial stopper 26, and capped by a metal band 27. The vial stopper 26 has a stopper thickness T adjacent the vial axis 20A. The vial body 21 defines a vial interior 28 containing either a powdered or liquid drug contents 29. The vial stopper 26 has an uppermost stopper surface 26A. The syringe 10 typically contains diluents for reconstituting the vial contents 29.

The fluid transfer device 30 is constituted by a female vial adapter 31 having a longitudinal adapter axis 31A and including a top wall 32, a downward depending flared skirt 33 with a multitude of flex members 34 for snap fitting onto the vial 20, a pointed tubular cannula 36 with a cannula tip 37 for puncturing the vial stopper 26, and a flow communication lumen 38 in flow communication with the cannula 36. The female vial adapter 31 includes a flow communication lumen 38 terminating in a female Luer lock connector 39 for sealing screw thread mounting of the syringe 10 thereon. The flex members 34 have a first portion 34A proximate the top wall 32 including an inwardly directed protuberance 41 for snap fitting under the vial rim 22 and a second portion 34B distal the top wall 32. The second portions 34B subtend an exterior obtuse angle relative to their first portions 34A. The flared skirt 33 assists in the mounting of the fluid transfer device 30 on the vial 20 but may lead to relative large eccentric misalignments as compared generally cylindrical shaped skirts.

FIGS. 3A to 3E show the process of snap fit mounting the fluid transfer device 30 onto the vial 20 with reference to a horizontal surface S, and the process of tear formation in the vial stopper 26.

Figures 3A, 3B, 3C:
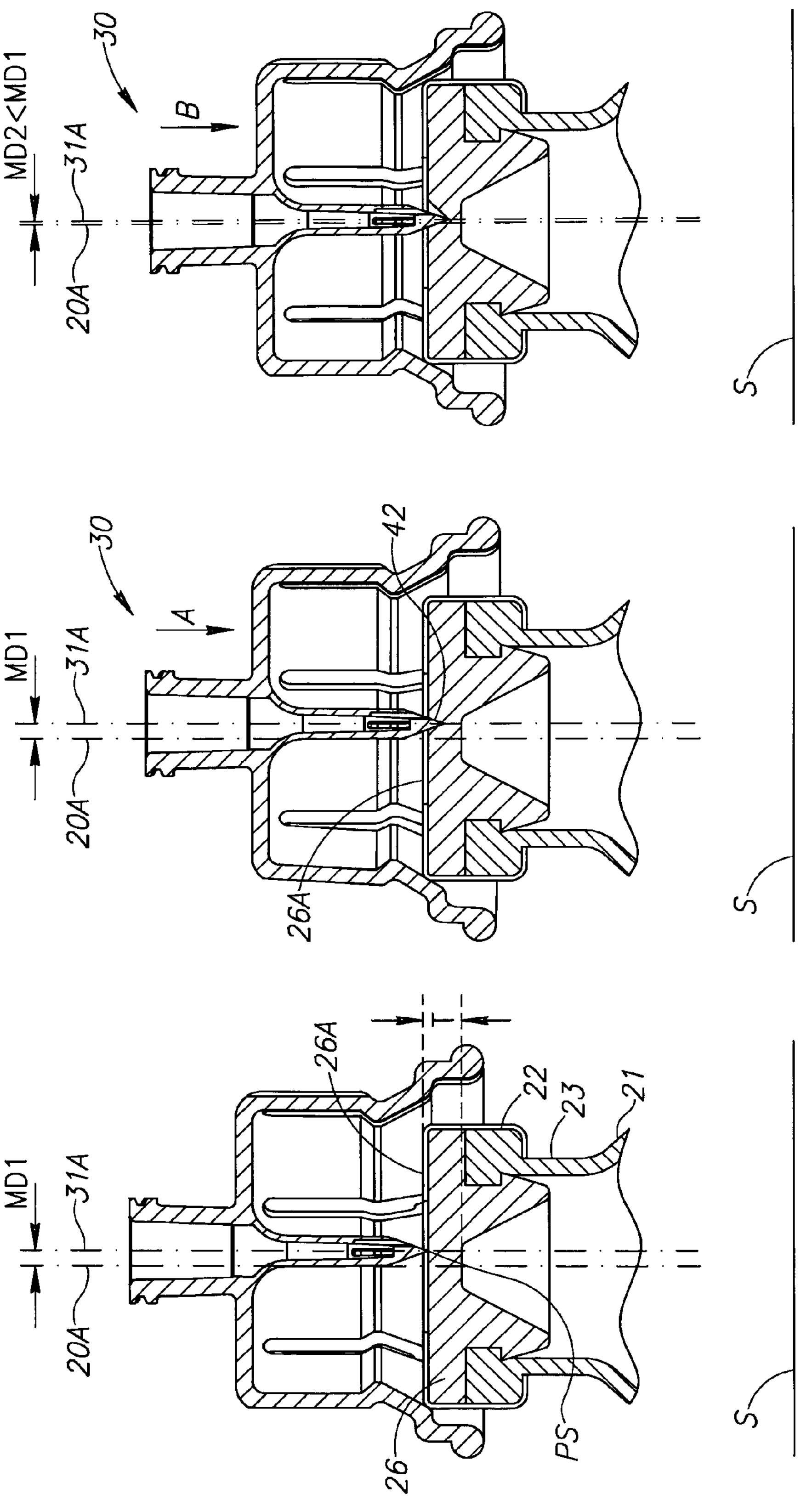
FIG.3A (PRIOR ART)
FIG.3B (PRIOR ART)
FIG.3C (PRIOR ART)
FIGS. 3A to 3E show the process of snap fit mounting FIG. 1's vial adapter onto a vial and the process of tear formation in its vial stopper due to an initial eccentric misalignment between the vial adapter and the vial.

FIG. 3A shows an initial stage of snap fit mounting the fluid transfer device 30 onto the vial 20 starting from an initial eccentric misalignment denoted by an initial misalignment distance MD1 between the vial axis 20A and the adapter axis 31A. The cannula tip 37 contacts the vial stopper 26 at a puncture site PS.

FIG. 3B shows a second stage of snap fit mounting the fluid transfer device 30 onto the vial 20. Depression of the vial adapter 31 towards the vial 20 denoted by arrow A causes its cannula tip 37 to start to penetrate the vial stopper 26 at the puncture site PS and the slight outward flexing of the leftmost flex member 34. The misalignment distance MD remains unchanged.

FIG. 3C shows a third stage of snap fit mounting the fluid transfer device 30 onto the vial 20. Further depression of the fluid transfer device 30 onto the vial 20 as denoted by arrow B causes the skirt 33 to align the fluid transfer device 30 with the vial 20 to reduce the misalignment distance to a reduced distance MD2 where MD2<MD1. Such alignment urges the cannula 36 towards the vial axis 20A which in turn causes the cannula tip 37 to begin a tear 42 in the uppermost stopper surface 26A.

Figure 3E:
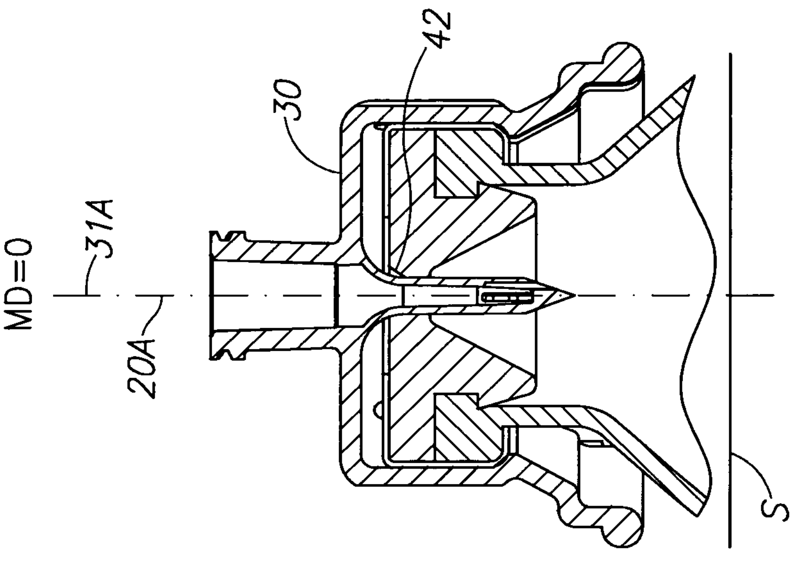
FIG.3E (PRIOR ART)
Figure 3D:
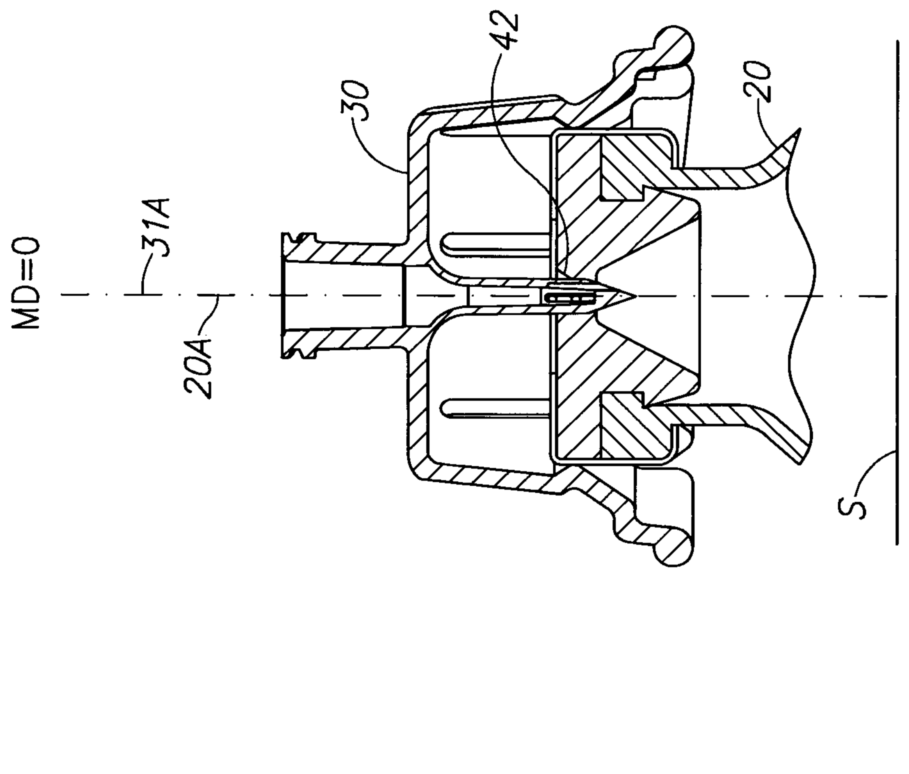
FIG.3D (PRIOR ART)
Figure 4:
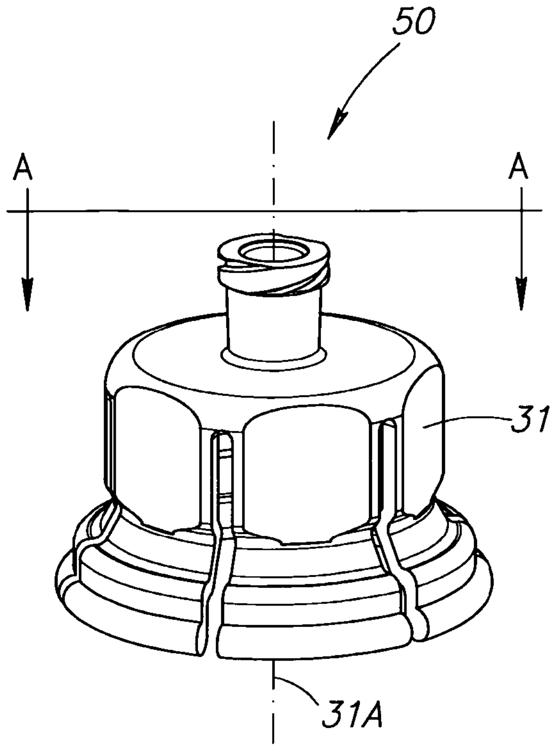
FIG. 4 is a front perspective view of a vial adapter including a sealing element in accordance with the present invention.
Figure 5:
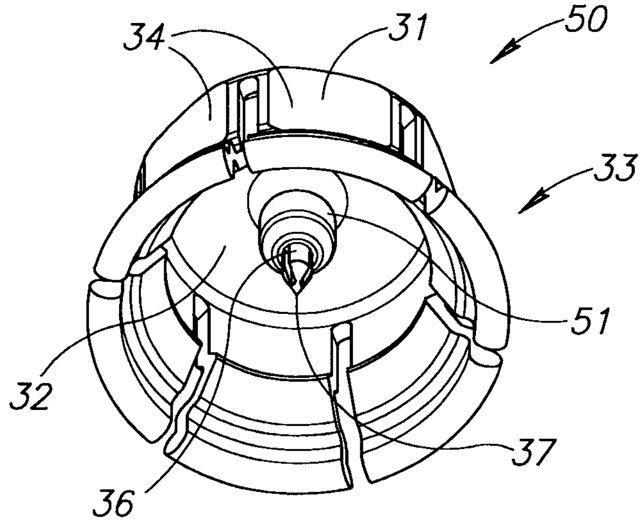
FIG. 5 is a bottom perspective view of FIG. 4's vial adapter.
Figure 6:
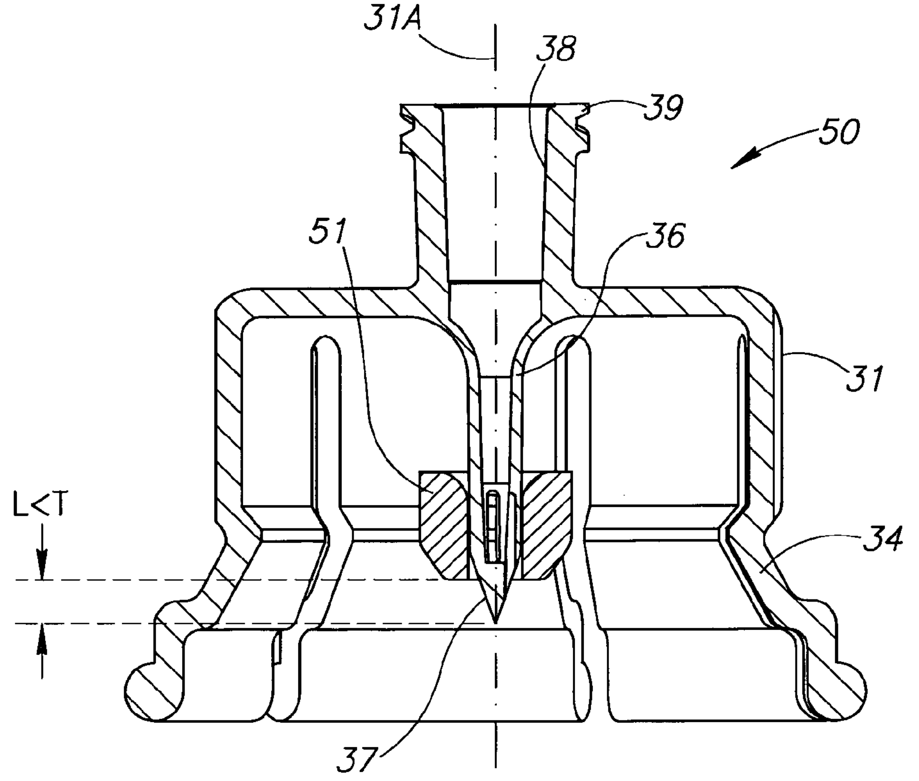
FIG. 6 is a longitudinal cross section of FIG. 4's vial adapter along line A-A therein showing its sealing element in its initial position.
Figure 7:
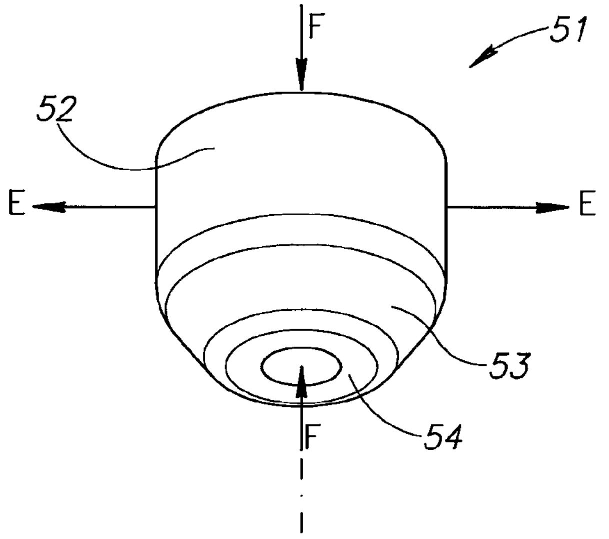
FIG. 7 is a close-up perspective view of FIG. 4's vial adapter's sealing element.

FIG. 3D shows a fourth stage of snap fit mounting the fluid transfer device 30 on the vial 20 in which the former 30 is fully concentric with the latter 20 and the cannula tip 37 has fully penetrated through the vial stopper 26 to establish flow communication with the vial interior 28 but prior to the fluid transfer device 30 snap fitting on the vial 20. The tear 42 may extend through the vial stopper 26 thereby creating a leakage path. The final misalignment distance MD is zero.

FIG. 3E shows the last stage of snap fit mounting the fluid transfer device 30 onto the vial 20 in which the flex members 34 snap fit onto the vial rim 22.

FIGS. 4 to 7 show a fluid transfer device 50 constituted by the female vial adapter 31 and therefore the same reference numbers are employed. The fluid transfer device 50 additionally includes an elastic O-ring like sealing element 51. The sealing element 51 is formed from relatively soft elastic material, for example, silicon, or other elastomeric material, which is considerably softer than the vial stopper 26. O-rings are generally considered to have a 60-90 hardness rating in the range of Shore A with 70 Shore A being the standard. The sealing element 51 is formed from relatively soft elastic material preferably less than 50 Shore A and in the range 5-35 Shore A. Manual application of an axial compression force F on the sealing element 51 causes the sealing element to expand outward in a radial direction E transversely to the axial compression force F to assume a flattened toroidal shape (see FIG. 8E).

The sealing element 51 has a tubular main body 52 and a converging tubular leading section 53 having a leading surface 54. The sealing element 51 is slidingly fitted onto the cannula 36 and disposed therealong towards the top wall 32 away from the cannula tip 37 to leave an exposed cannula length L between the leading surface 54 and the cannula tip 37. The exposed cannula length L is shorter than the stopper thickness T such that the sealing element 51 contacts the vial stopper 26 before the cannula 36 penetrates therethrough. The sealing element 51 sealingly encircles the cannula 36 to form a hermetic seal which is continuously maintained on slidingly urging the sealing element 51 towards the top wall 32 as opposed to rolling it theretoward as may occur with a harder Shore A rating.

Figure 8C:
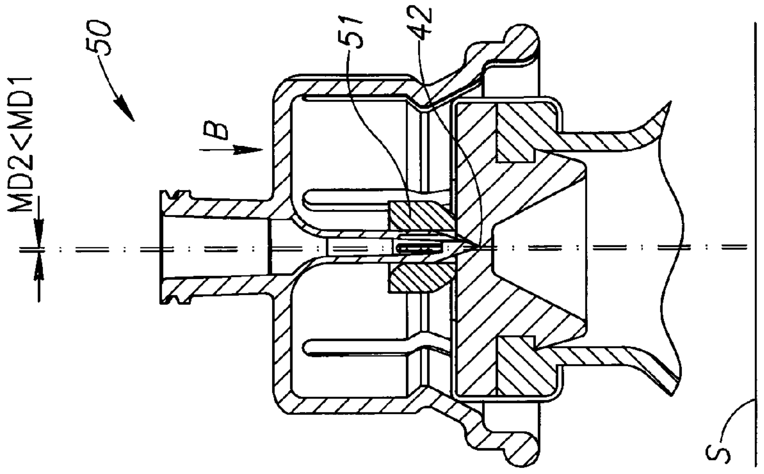
FIGS. 8A to 8E show the process of snap fit mounting FIG. 4's vial adapter onto a vial and its sealing element sealing any tears.
Figure 8B:
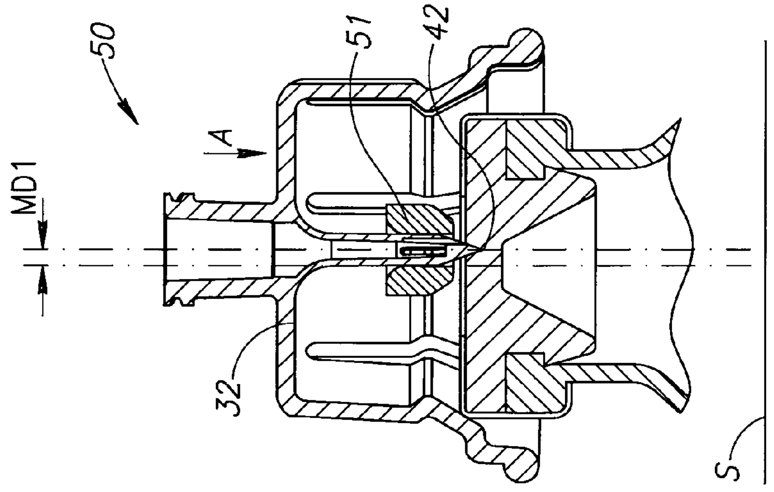
Figure 8A:
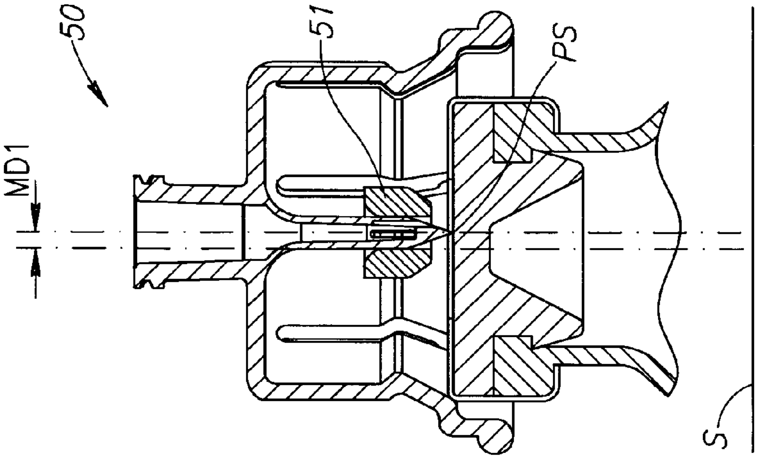
Figure 8E:
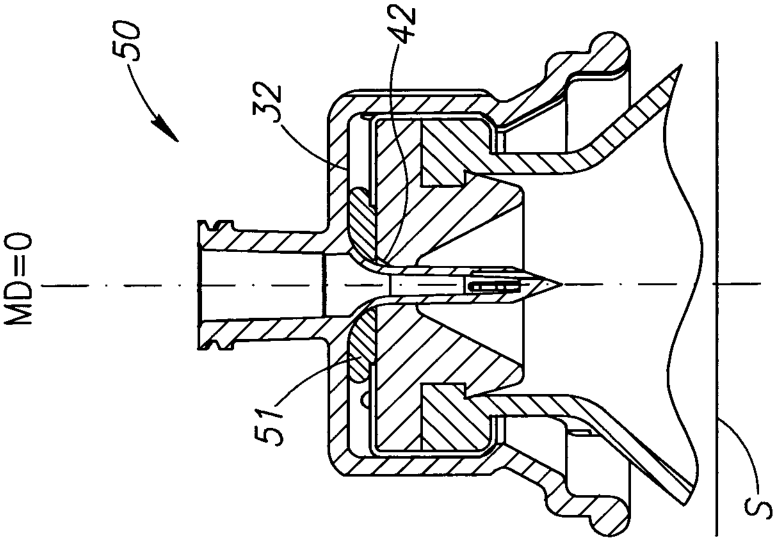
Figure 8D:
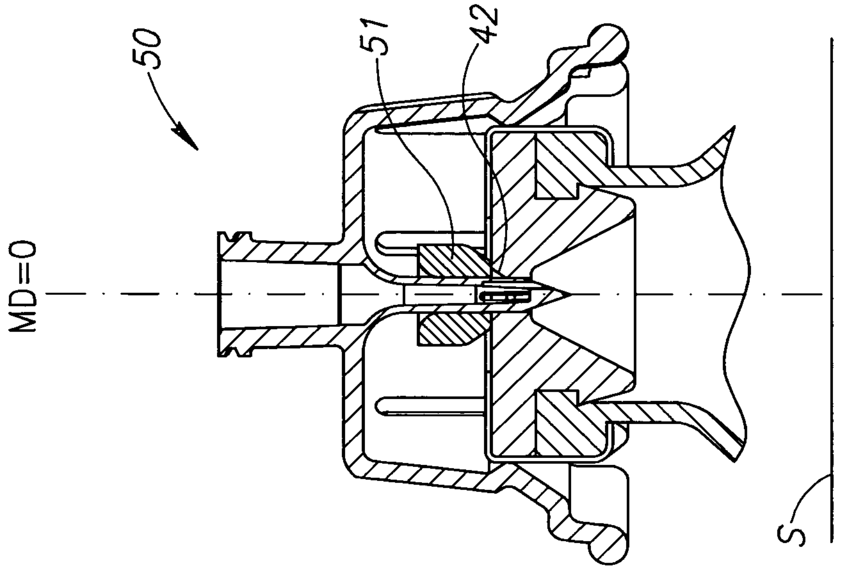

FIGS. 8A to 8E show the same steps as FIGS. 3A to 3E for snap fit mounting the fluid transfer device 50 onto the vial 20 for sealing the tear 42. FIG. 8A shows the cannula tip 37 contacting the stopper surface 26A at the puncture site PS and the sealing element 51 initially disposed above the stopper surface 26A. FIG. 8B shows the sealing element 51 approaching the stopper surface 26A as the cannula tip 37 starts to tear the vial stopper 26 starting from the puncture site PS. FIG. 8C shows the fluid transfer device 50 beginning to snap fit onto the vial 20 and the sealing element 51 sealing the puncture site PS and therefore the tear 42. FIG. 8D shows the sealing element 51 being slidingly urged towards the top wall 32 as the fluid transfer device 50 is depressed further onto the vial 20. The sealing element 51 continuously maintains a sealing encirclement of the cannula 36 and seals the puncture site PS. FIG. 8E shows the sealing element 51 being axially compressed between the top wall 32 and the stopper surface 26A on full snap fit mounting of the fluid transfer device 50 on the vial 20. The sealing element 51 is deformed into its compressed toroidal shape and continues to seal the tear 42.

Figure 9:
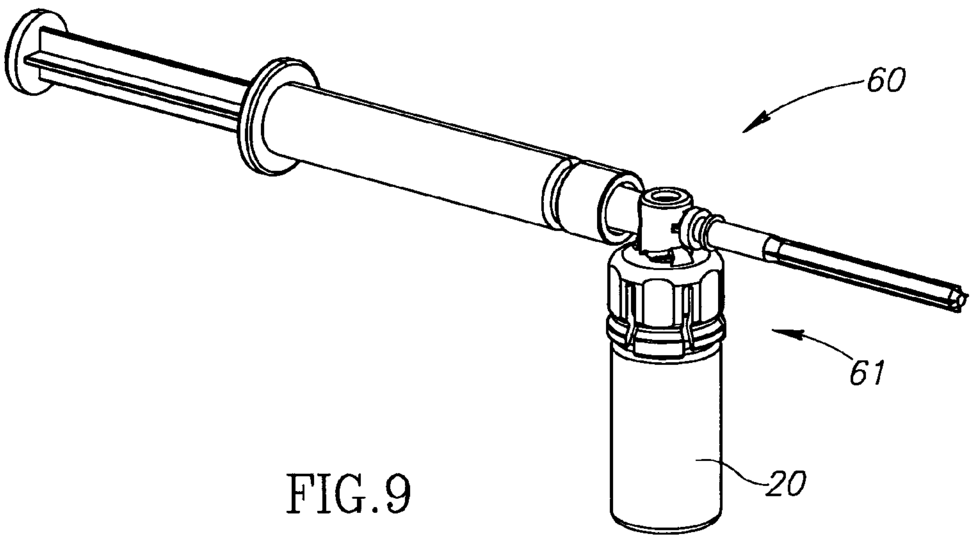
FIG. 9 is a pictorial representation of Applicant's MIXJECT® fluid transfer device including a vial adapter snap fit mounted onto a vial.
Figure 10:
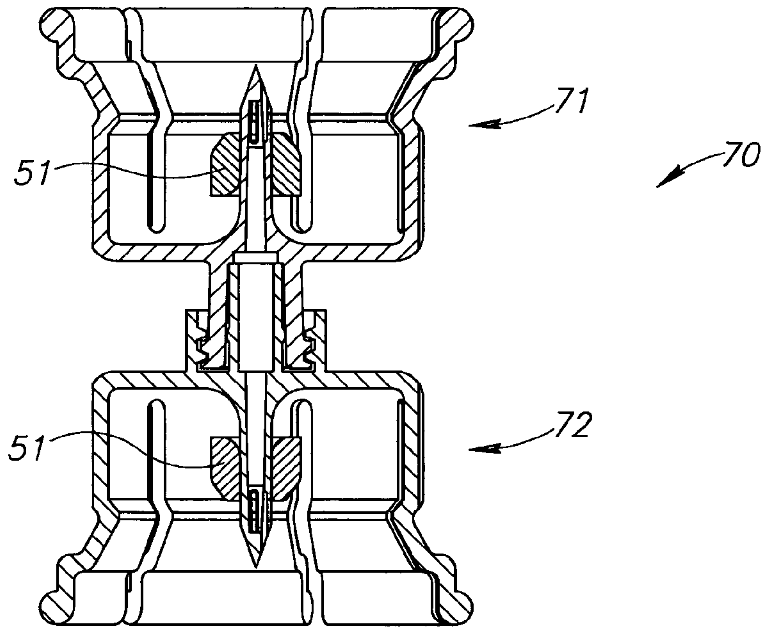
FIG. 10 is a longitudinal cross section of Applicant's MIX2VIAL® fluid transfer assemblage including a male vial adapter and a female vial adapter each fitted with a sealing element.

FIG. 9 show a pictorial representation of a MIXJECT® fluid transfer control device 60 including a vial adapter 61 snap fitted onto a vial 20. The vial adapter 61 can be fitted with a sealing element 51. FIG. 18 shows a longitudinal cross section of a MIX2VIAL® fluid transfer assemblage 70 including a male vial adapter 71 and a female vial adapter 72 similar to the female vial adapter 31. The vial adapters 71 and 72 can each be fitted with a sealing element 51.

While the invention has been described with respect to a limited number of embodiments, it will be appreciated that many variations, modifications, and other applications of the invention can be made within the scope of the appended claims.

The invention claimed is:

1. A fluid transfer device for use with a medicinal vial having a longitudinal vial axis and including a vial body having a vial interior for storing a medicament, a vial rim defining a vial opening, a narrow neck intermediate the vial body and the vial rim, a vial stopper sealing the vial opening and having a stopper thickness T close to the vial axis, the vial stopper having an uppermost stopper surface, the fluid transfer device comprising:

a) a vial adapter having a longitudinal adapter axis and including a top wall transverse to said adapter axis, a downward depending skirt with flex members configured to be snap fitted onto the vial rim for concentric mounting of said vial adapter on the vial, a tubular cannula having a pointed tip configured to initially contact the vial stopper at a puncture site and puncture therethrough for establishing flow communication with the vial interior on said snap fit mounting, and a flow communication channel in flow communication with said cannula; and b) an elastic O-ring like sealing element sealingly encircling said cannula and being slidably disposed on said cannula, said sealing element being initially disposed along said cannula and spaced apart from said top wall and said pointed tip to leave a first exposed cannula length L between said sealing element and said pointed tip and a second exposed cannula length between said sealing element and said top wall, said first exposed cannula length L being shorter than said stopper thickness T such that said sealing element contacts the vial stopper prior to said cannula puncturing therethrough, said sealing element being configured to be brought into initial contact with the vial stopper subsequent to said pointed tip contacting the vial stopper at said puncture site and to be thereafter slidingly urged on said cannula toward said top wall and continuously seal said puncture site during said snap fit mounting of said vial adapter on the vial.

2. The device according to claim 1, wherein said sealing element includes a tubular main body and a converging tubular leading section facing towards said pointed tip.

3. The device according to claim 1, wherein said sealing element deforms in a radial direction when axially compressed between said top wall and the uppermost stopper surface.

4. The device according to claim 1, wherein said sealing element has a hardness rating less than 50 Shore A.

5. The device according to claim 1, wherein said sealing element has a hardness rating in a range of 5 to 35 Shore A.

6. A fluid transfer device for use with a medicinal vial having a longitudinal vial axis and including a vial body having a vial interior for storing a medicament, a vial rim defining a vial opening, a narrow neck intermediate the vial body and the vial rim, a vial stopper sealing the vial opening and having a stopper thickness T close to the vial axis, the vial stopper having an uppermost stopper surface and an opposing bottommost stopper surface, the fluid transfer device comprising:

a) a vial adapter having a longitudinal adapter axis and including a top wall transverse to said adapter axis, a downward depending skirt with flex members configured to be snap fitted onto the vial rim for concentric mounting of said vial adapter on the vial, a tubular cannula having a pointed tip configured to initially contact the vial stopper at a puncture site and puncture therethrough to establish flow communication with the vial interior on said snap fit mounting, and a flow communication channel in flow communication with said cannula; and b) an elastic O-ring like sealing element sealingly encircling said cannula and being configured to slide on said cannula, said sealing element being initially disposed along said cannula and spaced apart from said top wall and said pointed tip to leave an exposed cannula length L between said sealing element and said pointed tip, said sealing element being configured to be brought into initial contact with the vial stopper subsequent to said pointed tip contacting the vial stopper at said puncture site and to be thereafter slidingly urged on said cannula toward said top wall and continuously seal said puncture site during said snap fit mounting of said vial adapter on the vial, such that said sealing element is configured to contact the uppermost stopper surface before the pointed tip pierces the bottommost stopper surface to prevent vacuum leakage.

7. The device according to claim 6, wherein said sealing element includes a tubular main body and a converging tubular leading section facing towards said pointed tip.

8. The device according to claim 6, wherein said sealing element deforms in a radial direction when axially compressed between said top wall and the uppermost stopper surface.

9. The device according to claim 6, wherein said sealing element has a hardness rating less than 50 Shore A.

10. The device according to claim 6, wherein said sealing element has a hardness rating in a range of 5 to 35 Shore A.

* * * * *